United States Patent
Al-Oboudi

(10) Patent No.: US 10,441,452 B1
(45) Date of Patent: Oct. 15, 2019

(54) SHOULDER ROTATION DEVICE

(71) Applicant: Waleed Al-Oboudi, San Diego, CA (US)

(72) Inventor: Waleed Al-Oboudi, San Diego, CA (US)

( * ) Notice: Subject to any disclaimer, the term of this patent is extended or adjusted under 35 U.S.C. 154(b) by 451 days.

(21) Appl. No.: 14/636,100

(22) Filed: Mar. 2, 2015

Related U.S. Application Data

(60) Provisional application No. 61/946,616, filed on Feb. 28, 2014.

(51) Int. Cl.
| | | |
|---|---|---|
| *A61F 5/01* | (2006.01) | |
| *A61F 5/37* | (2006.01) | |
| *A61H 1/02* | (2006.01) | |

(52) U.S. Cl.
CPC ............ *A61F 5/013* (2013.01); *A61F 5/3723* (2013.01); *A61F 5/3738* (2013.01); *A61H 1/0281* (2013.01); *A61H 2001/0203* (2013.01)

(58) Field of Classification Search
CPC ...... A61F 5/0102; A61F 5/0104; A61F 5/013; A61F 2005/0151; A61F 2005/0153; A61F 5/058; A61F 5/05825; A61F 5/05858; A61F 5/37; A61F 5/3723; A61F 5/373; A61F 5/3738; A61F 13/04; A61F 13/10; A61F 13/101; A61F 5/0113; A61F 5/0111; A61F 5/0118; A61F 5/05866; A61F 5/3761; A61F 2005/0158; A61F 2005/0197; A61H 1/02; A61H 1/0274; A61H 1/0277; A61H 1/0281; A61H 2001/0203; A61H 2203/0456; A63B 23/1245; A63B 23/1254; A63B 23/03508; A63B 2208/0252

See application file for complete search history.

(56) References Cited

U.S. PATENT DOCUMENTS

| | | | | |
|---|---|---|---|---|
| 1,643,850 | A * | 9/1927 | Jones ................. | A61F 5/05858 602/16 |
| 5,337,737 | A * | 8/1994 | Rubin ................ | A63B 23/1281 128/898 |
| 5,919,148 | A * | 7/1999 | Marko ................ | A61B 5/0488 402/8 |

(Continued)

OTHER PUBLICATIONS

Fulcrum—Definition. (n.d.). Retrieved Jun. 26, 2017, from https://en.oxforddictionaries.com/definition/fulcrum.*

(Continued)

*Primary Examiner* — Alireza Nia
*Assistant Examiner* — Rachel A Berezik
(74) *Attorney, Agent, or Firm* — Knobbe Martens Olson & Bear LLP

(57) ABSTRACT

A therapy aid device for improving rotation of shoulder complex is provided. The device includes an upper portion and a lower portion joined together by an angled connector. The upper portion is configured to attach to a user's upper arm and the lower portion is configured to attach to the user's lower arm. The lower portion may also be configured to keep a user's hand in a flexed angled position. Using the device, the user may rotate the shoulder and move while keeping the upper and lower arms and wrist in specific positions. For example, the user may rotate his shoulder such that the user's hand and forearm move away from the torso while the elbow generally remain in the same location.

14 Claims, 14 Drawing Sheets

(56) References Cited

U.S. PATENT DOCUMENTS

| | | | | |
|---|---|---|---|---|
| 5,951,499 | A | * | 9/1999 | Saringer .............. A61H 1/0274 601/33 |
| 8,852,063 | B2 | * | 10/2014 | Bua ...................... A61H 1/0281 482/139 |
| 2003/0125651 | A1 | * | 7/2003 | Hopkins ................. A61F 5/013 602/20 |
| 2007/0055191 | A1 | * | 3/2007 | Farrell ................ A61F 5/05866 602/21 |
| 2008/0312053 | A1 | * | 12/2008 | Kay ..................... A61H 1/0281 482/124 |
| 2013/0090580 | A1 | * | 4/2013 | Hong ................... A61H 1/0277 601/33 |

OTHER PUBLICATIONS

Fulcrum. The Free Dictionary online, definition 2, https://www.thefreedictionary.com/fulcrum.*

* cited by examiner

SHOULDER ROTATION DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The invention generally relates to orthotic devices, and more particularly to a device the can be used as a therapy aid to help improve mobility of the shoulder complex.

Description of the Related Art

A patient's shoulder mobility can be greatly affected due to stroke, brain injury or other illnesses. Various other medical conditions can also cause decreased mobility of the shoulder complex. There is a need for a device that can be used as a therapy aid to help patients recover or improve shoulder mobility.

SUMMARY OF THE INVENTION

The systems, methods and devices described herein have innovative aspects, no single one of which is indispensable or solely responsible for their desirable attributes. Without limiting the scope of the claims, some of the advantageous features will now be summarized.

In some embodiments of the shoulder rotation device, the device may comprise a upper portion and a lower portion, which are at least temporarily attached to a connector. The connector may comprise an angle and may comprise a 90° angle. The upper portion may be configured to attached to or engage a user's upper arm, for instance between the user's elbow and shoulder. The upper portion may comprise straps or another attachment mechanism. The lower portion may be configured to attach to or engage a user's lower arm, for instance between the user's elbow and hand. The lower portion may be configured to substantially keep the user's hand, wrist, and/or fingers in a specific position. The lower portion may comprise straps or another attachment mechanism. The lower portion may be configured to keep a user's hand, when engaged with the rotation device, flexed or stretched out. The device may be used in multiple positions, which may comprise the user lying on his back with the rotation device engaged to at least part of the user's arm. The user may perform movements or exercises at least, wherein the user begins with his elbow near his waist and his hand generally up in the air. The user may then rotate his shoulder outwards such that the user's hand moves away from the user's torso. The user may then rotate his arm back to or near the starting position. The rotation device may benefit the user in performing certain movements or exercises, as it may substantially keep parts of the user's body, including the user's arm, hand, wrist, and/or fingers, in a specific position, which may be beneficial to the user during the movements or exercises.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting. Like reference numbers and designations in the various drawings indicate like elements. Not all of the elements of the drawings are in to scale relate to other drawings and the comparative size of one element relative to another element in the drawings is not necessarily indicative of the relative sizes of the elements in one or more embodiments.

DETAILED DESCRIPTION OF THE PREFERRED EMBODIMENT

Figure 1:
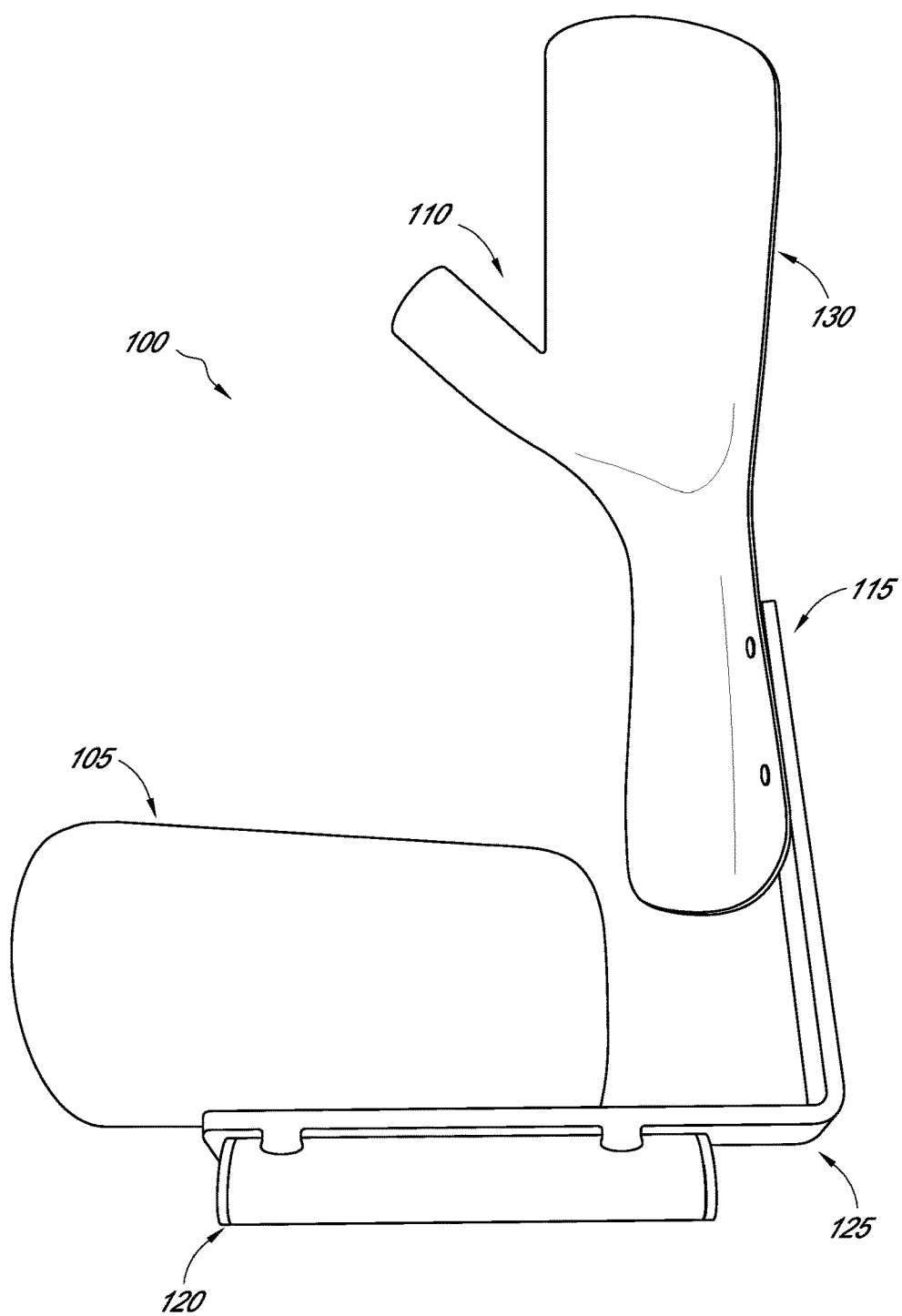
FIG. 1 illustrates a front view of a first embodiment of a rotation device.
Figure 2:
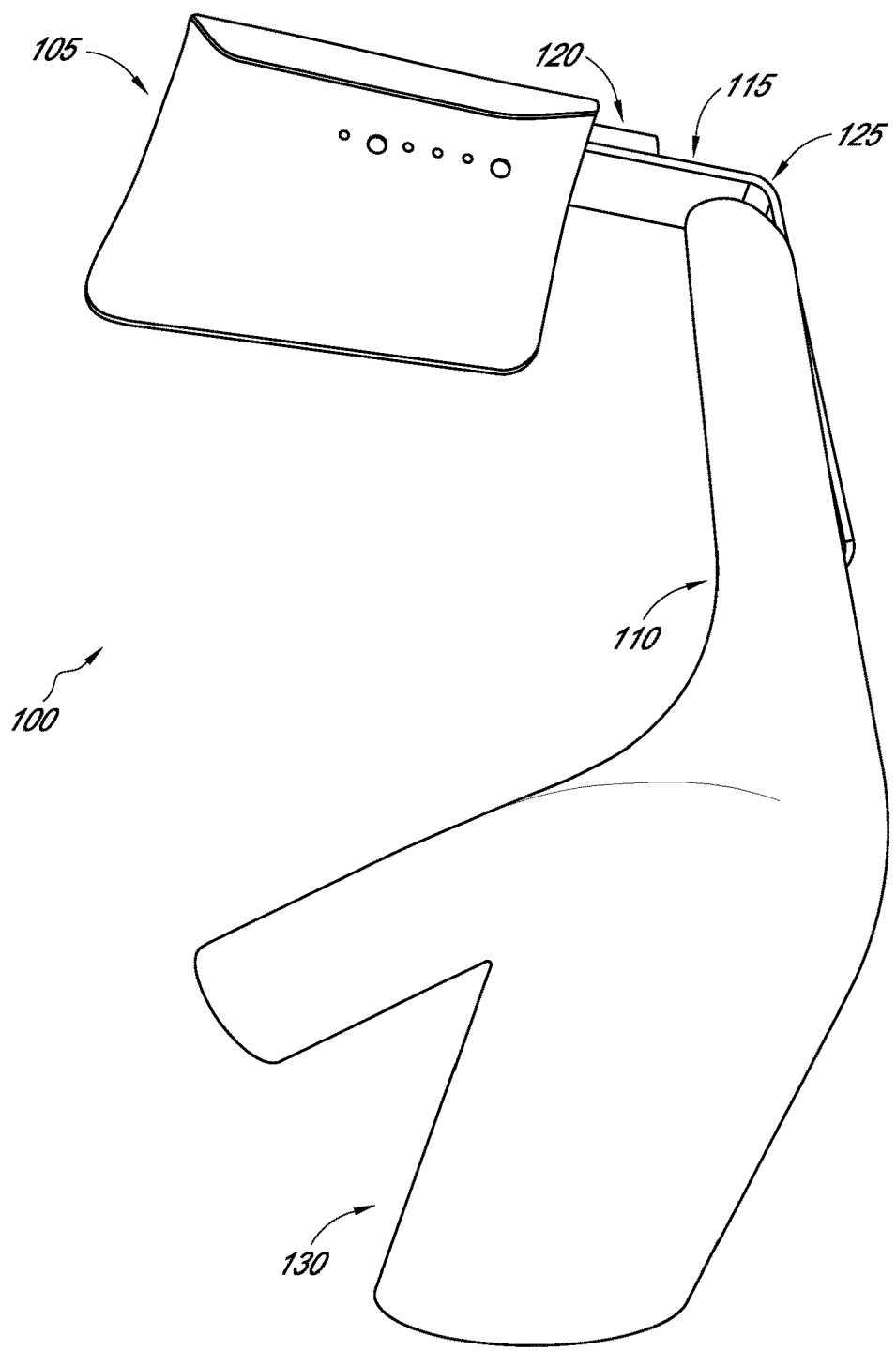
FIG. 2 illustrates an end perspective view of a first embodiment of a rotation device.
Figure 3:
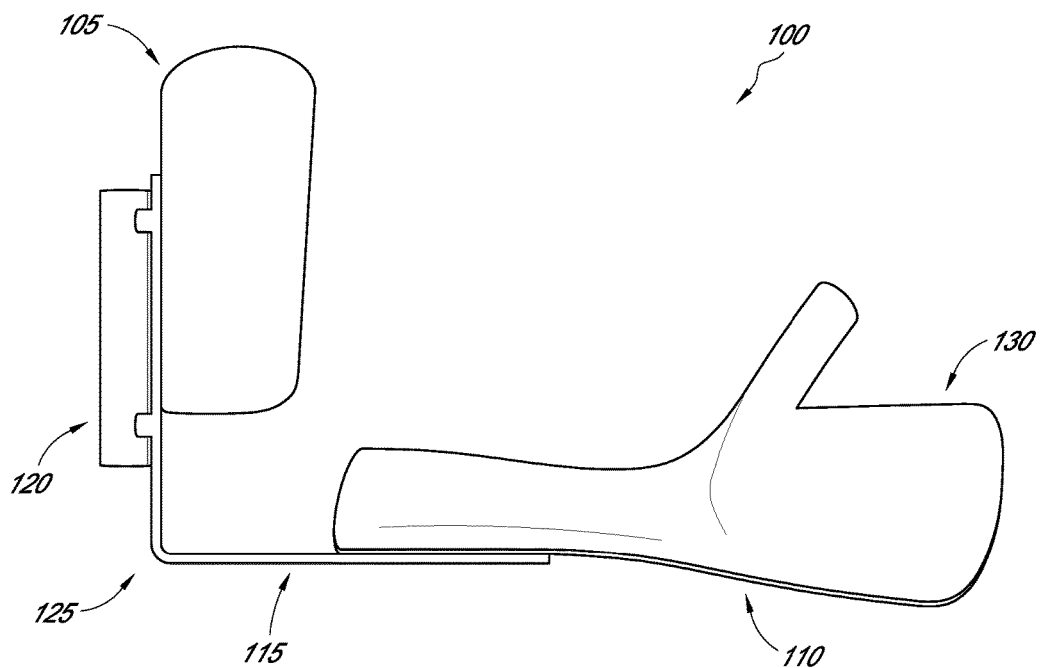
FIG. 3 illustrates a front view of a first embodiment of a rotation device.
Figure 4:
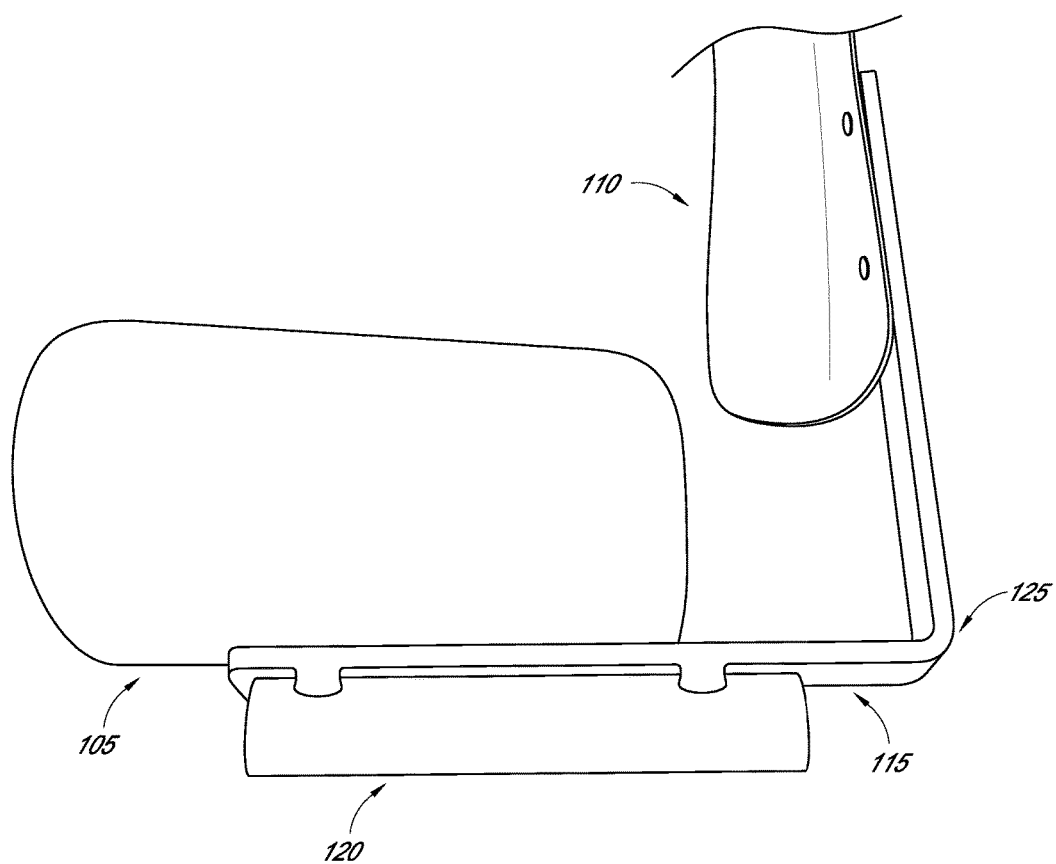
FIG. 4 illustrates a front view of part of a first embodiment of a rotation device.

In the following detailed description, reference is made to the accompanying drawings, which form a part of the present disclosure. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure. For example, a system or device may be implemented or a method may be practiced using any number of the aspects set forth herein. In addition, such a system or device may be implemented or such a method may be practiced using other structure, functionality, or structure and functionality in addition to or other than one or more of the aspects set forth herein. Elements that are described as "connected," "engaged," "attached," or similarly described, shall include being directly and/or indirectly connected, engaged, attached, etc. Alterations and further modifications of the inventive features illustrated herein, and additional applications of the principles of the inventions as illustrated herein, which would occur to one skilled in the art and having possession of this disclosure, are to be considered within the scope of the invention.

Descriptions of unnecessary parts or elements may be omitted for clarity and conciseness, and like reference numerals refer to like elements throughout. In the drawings, the size and thickness of layers and regions may be exaggerated for clarity and convenience.

Features of the present disclosure will become more fully apparent from the following description, taken in conjunction with the accompanying drawings. It will be understood these drawings depict only certain embodiments in accordance with the disclosure and, therefore, are not to be considered limiting of its scope; the disclosure will be described with additional specificity and detail through use of the accompanying drawings. An apparatus, system or method according to some of the described embodiments can have several aspects, no single one of which necessarily is solely responsible for the desirable attributes of the apparatus, system or method. After considering this discussion, and particularly after reading the section entitled "Detailed Description" one will understand how illustrated features serve to explain certain principles of the present disclosure.

As shown in FIGS. 1-6, in some embodiments the rotation device 100 comprises an upper arm portion 105 and a lower arm portion 110. The device may also comprise a connector 115 that connects the upper arm portion 105 and lower arm portion 110. The rotation device may also comprise a fulcrum portion 120. The upper arm portion 105 may comprise a surface that engages with a user's upper arm such as the shoulder, the bicep, or the tricep. The upper arm portion 105 may be configured such that it cradles or otherwise engages the upper arm of the user, and at least parts of the upper arm portion may comprise shapes such as a trough or semi-cylinder. The upper arm portion 105 may be configured such that a first side extends further away from the connector 115 than does the second side. The first side may extend generally straight up away from the connector 115, or may curve in one direction or another. In some embodiments, the first side of the upper arm portion 105 in the side that may contact the outside of the user's arm.

The lower arm portion 110 may comprise a hand section 130 that engages the user's hand and/or wrist. The lower arm portion 110 may be configured to isolate the user's hand and/or wrist in a specific position. Parts of the lower arm portion 110 may be curved such that they contact the users arm in more than one place. For instance, the lower arm portion 110 may wrap at least partially around the users arm when engaged to the users arm. The hand portion 130 may be curved such that at least part of the hand portion wraps around at least part of the hand of the user. The part of the hand portion 130 that engages the users thumb, may wrap around at least part of the users thumb. The parts of the upper arm portion 105, lower arm portion 110, and hand portion 130 that curve or wraparound at least part of the user's hand or arm, may help keep the users hand or arm in the desired position during exercises and/or movements.

Figure 5:
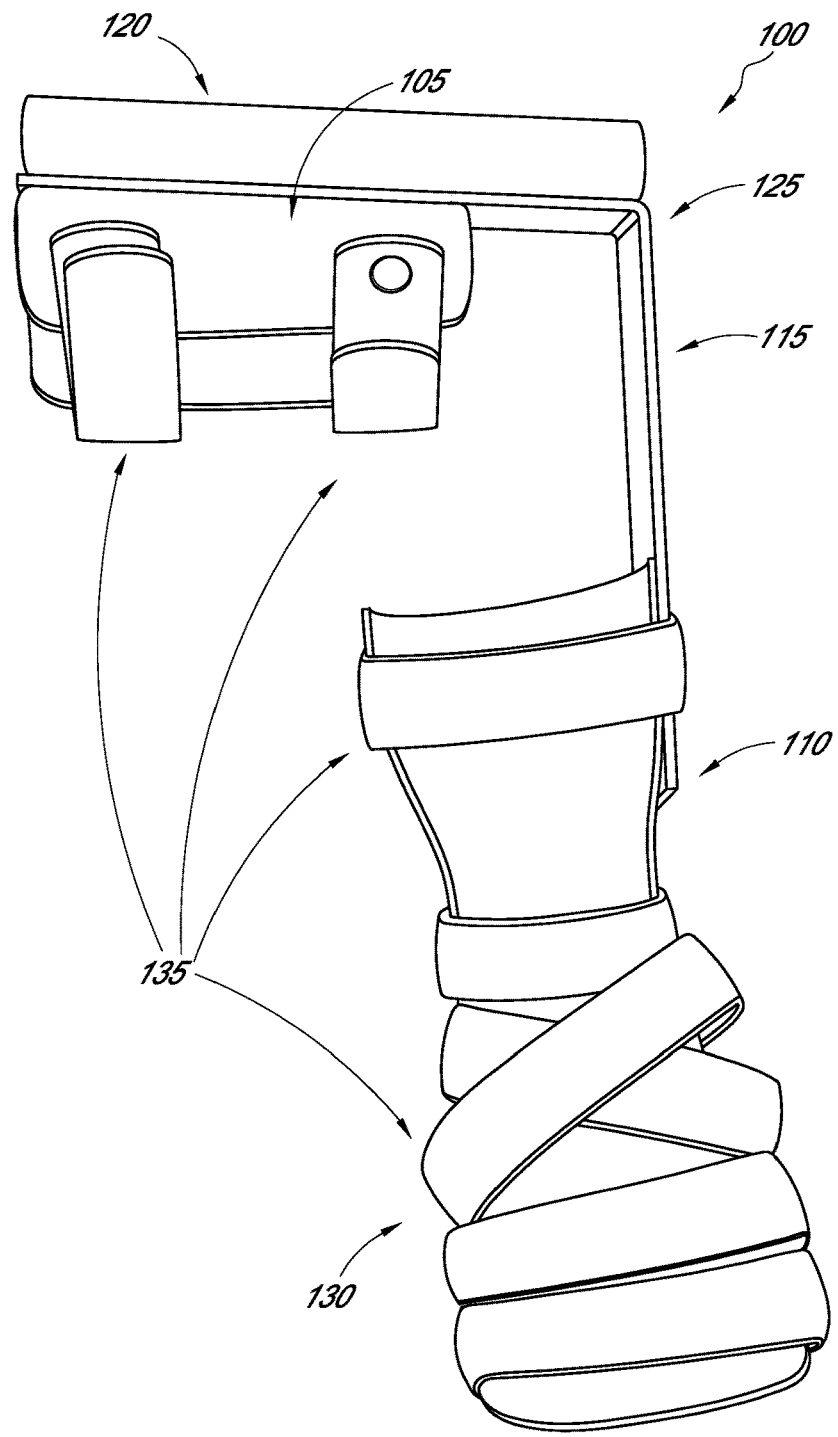
FIG. 5 illustrates a front view of a second embodiment of a rotation device.
Figure 6:
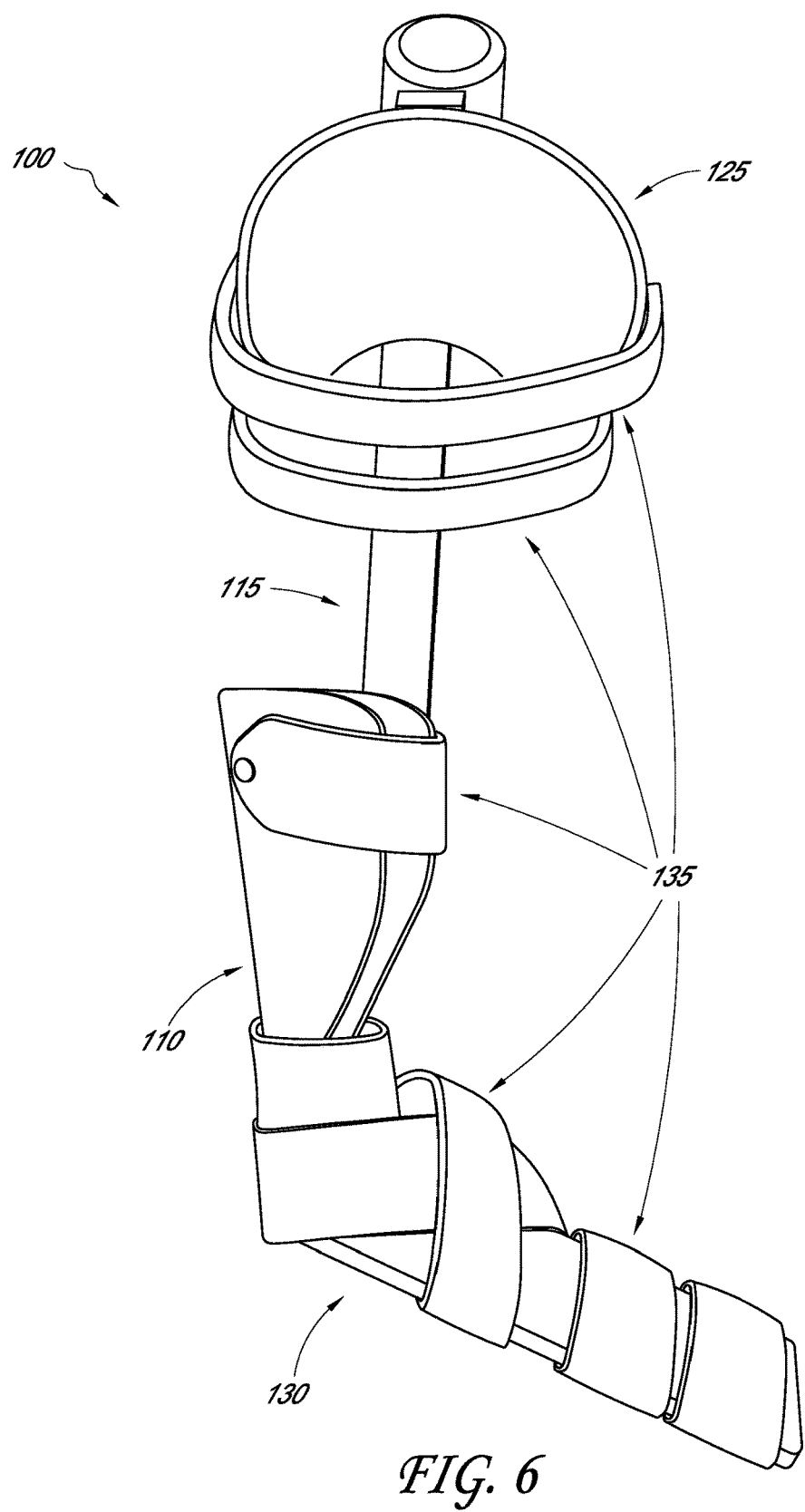
FIG. 6 illustrates a top view of a second embodiment of a rotation device.

The upper arm portion 105 and the lower arm portion 110 may be attached to a connector 115 that may comprise an approximately 90° bend 125. Also attached to the connector 115 may be a fulcrum portion 120 that is generally opposite the upper arm portion 105 on the connector 115. The rotation device 100 may also comprise one or more straps 135 located on the upper arm portion 105, the lower arm portion 110, or some other part of the rotation device 100 (as shown in FIGS. 5 and 6). The straps 135 may be configured to go around or encircle at least part of a user's arm and temporarily secure the user's arm to at least part of the rotation device 100. The straps 135 may also go around or encircle the user's wrist, hand, and/or fingers, in order to secure those parts of the user's arm to at least part of the rotation device 100.

As shown in FIGS. 7-14, in some embodiments, the rotation device 100 is used by a user that is lying on his back.

Figure 7:
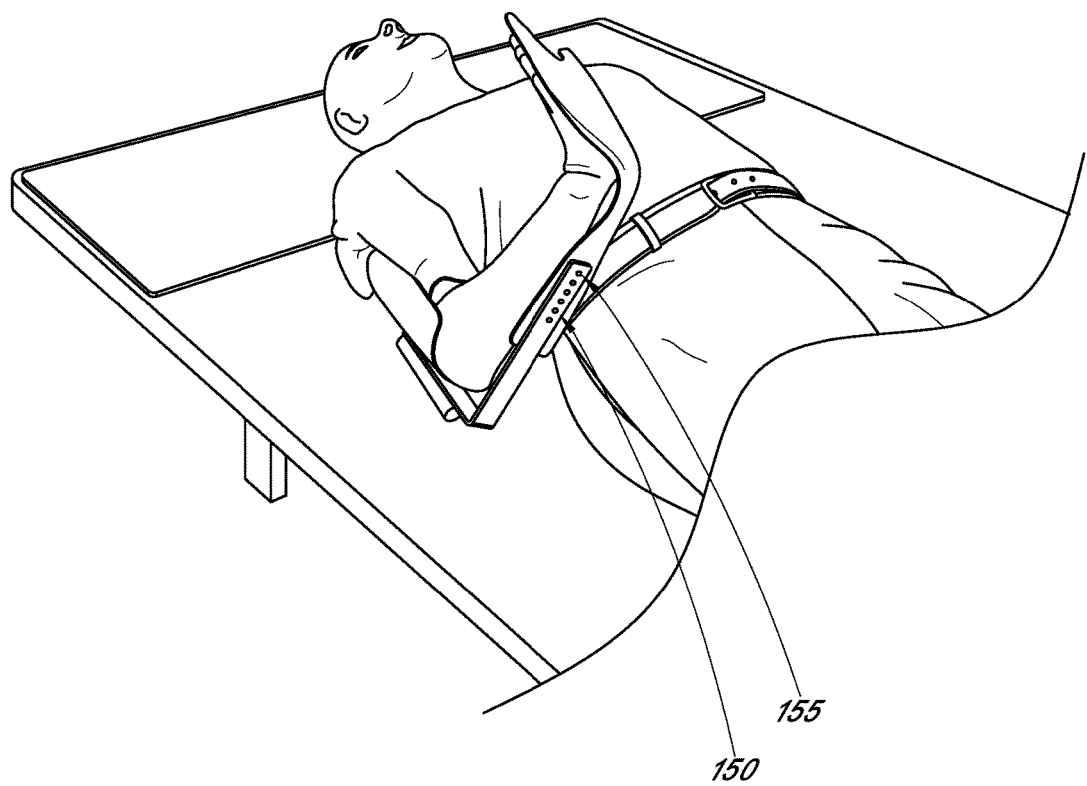
FIG. 7 illustrates a method of use of a rotation device.
Figure 8:
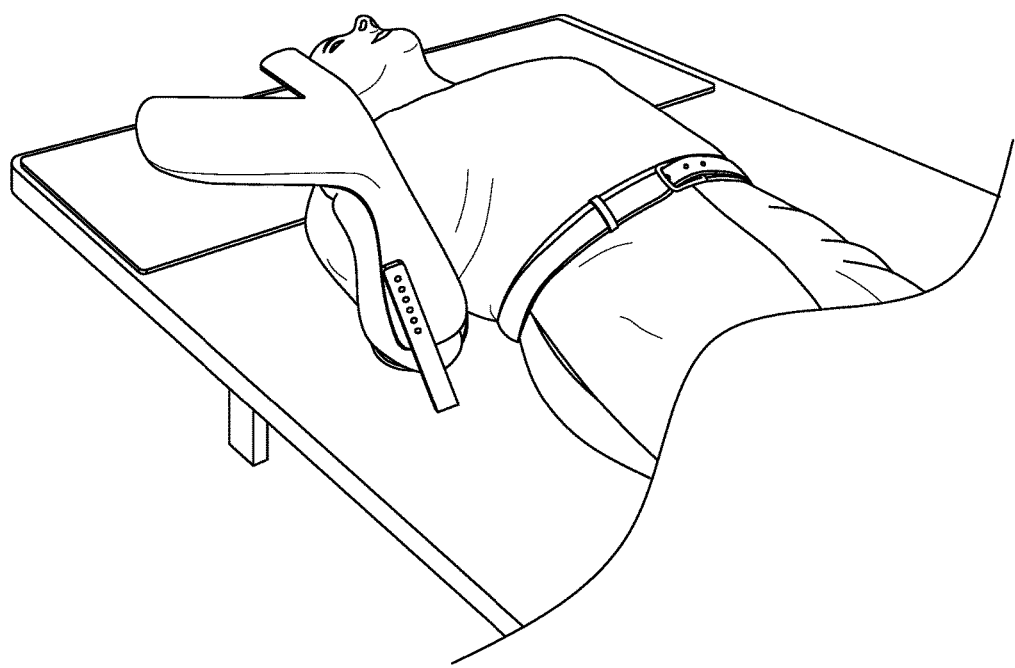
FIG. 8 illustrates a method of use of a rotation device.
Figure 9:
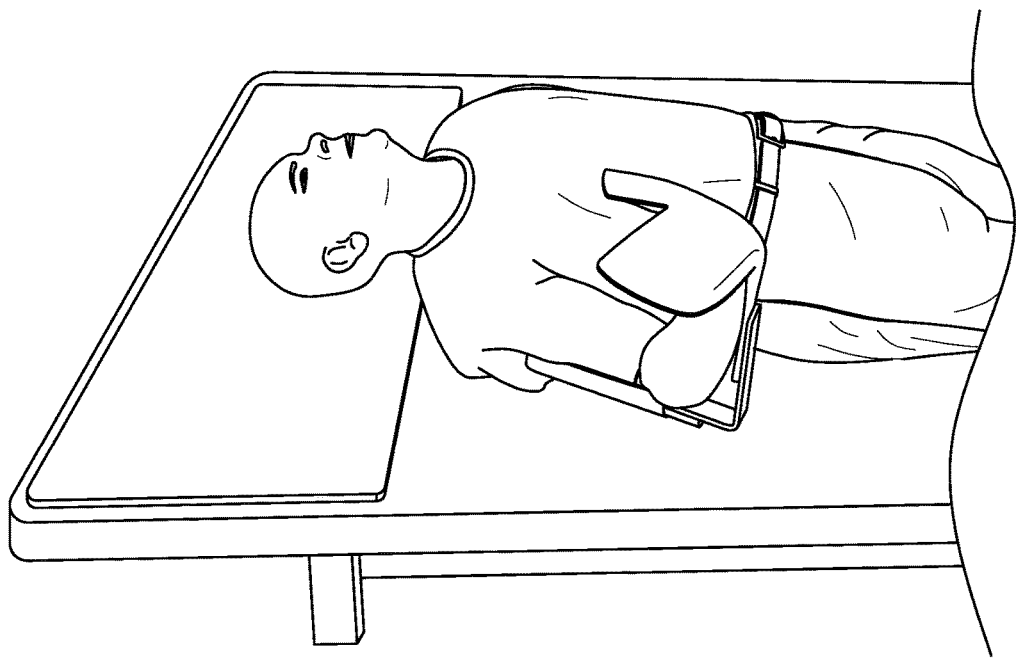
FIG. 9 illustrates a method of use of a rotation device.
Figure 10:
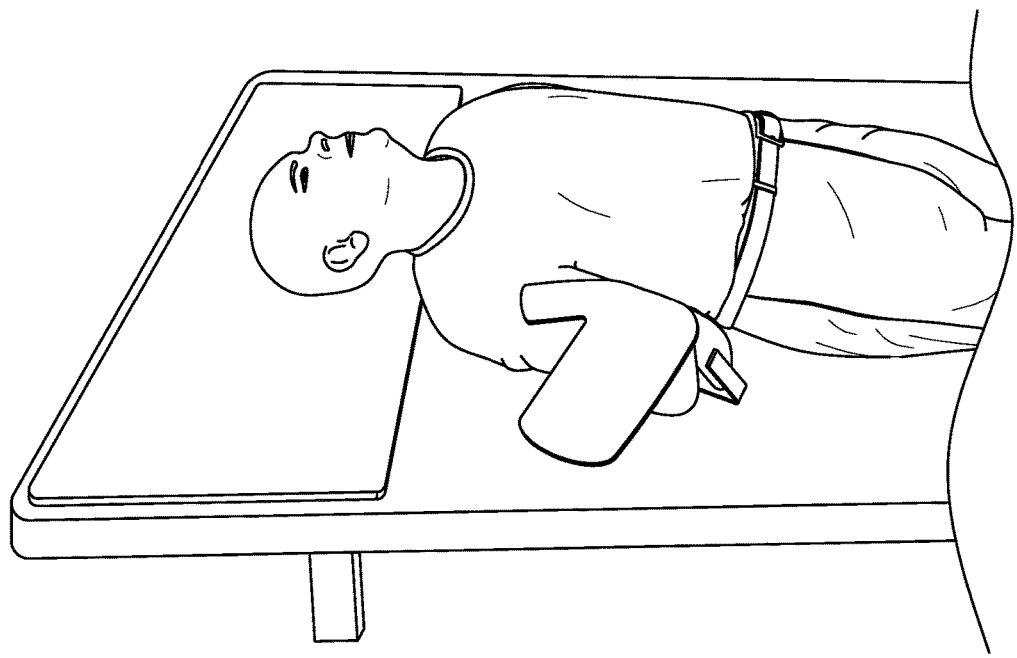
FIG. 10 illustrates a method of use of a rotation device.
Figure 11:
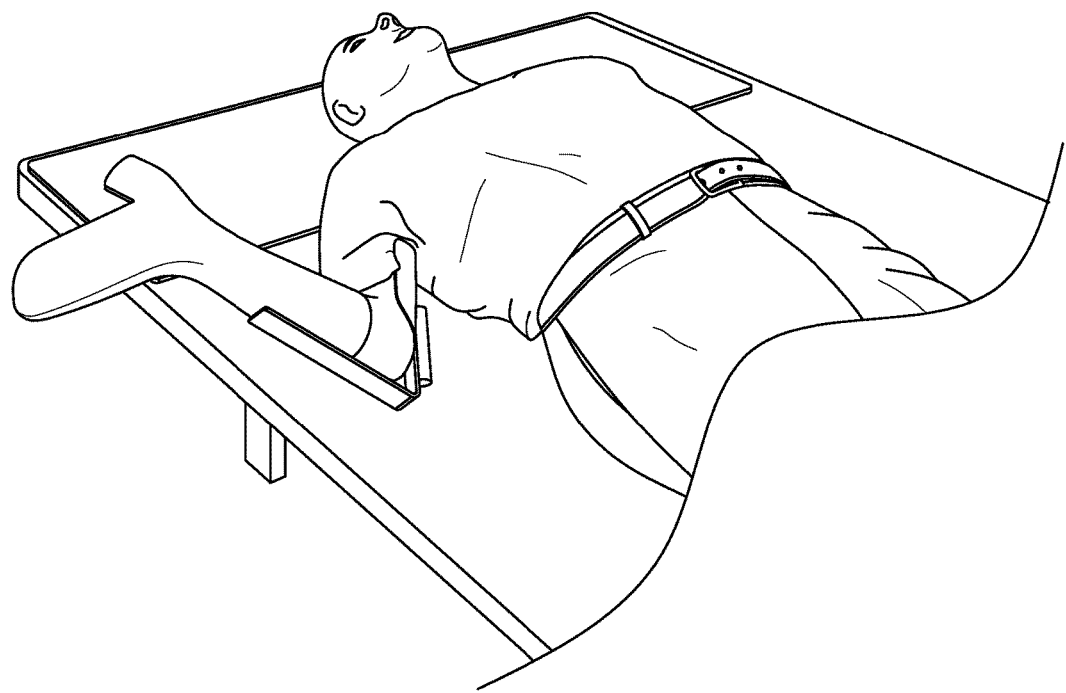
FIG. 11 illustrates a method of use of a rotation device.
Figure 12:
FIG. 12 illustrates a method of use of a rotation device.
Figure 13:
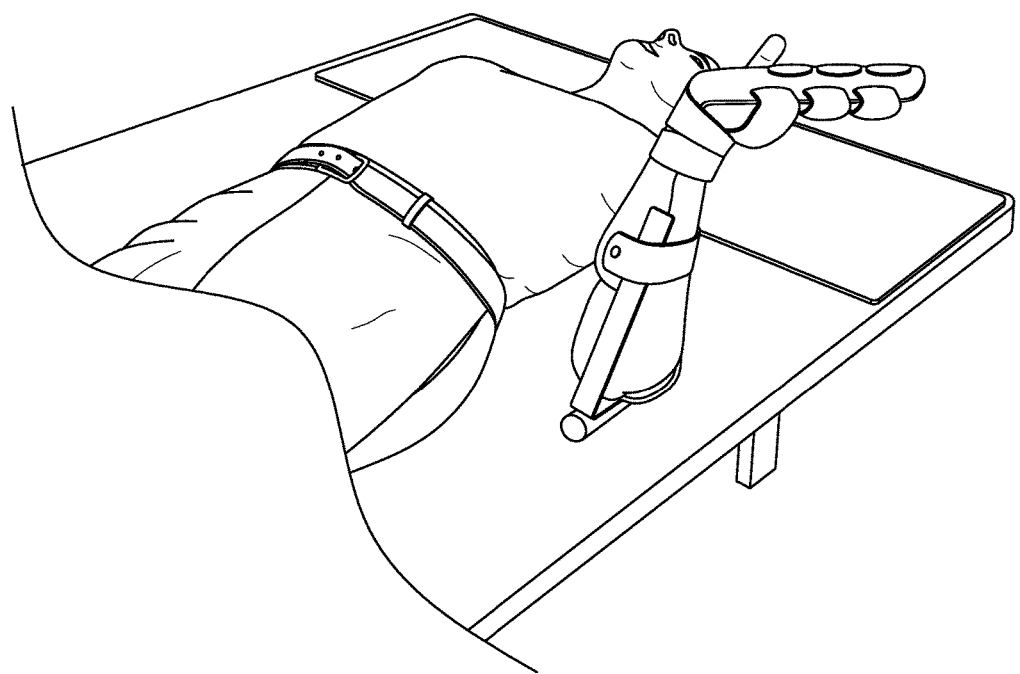
FIG. 13 illustrates a method of use of a rotation device.
Figure 14:
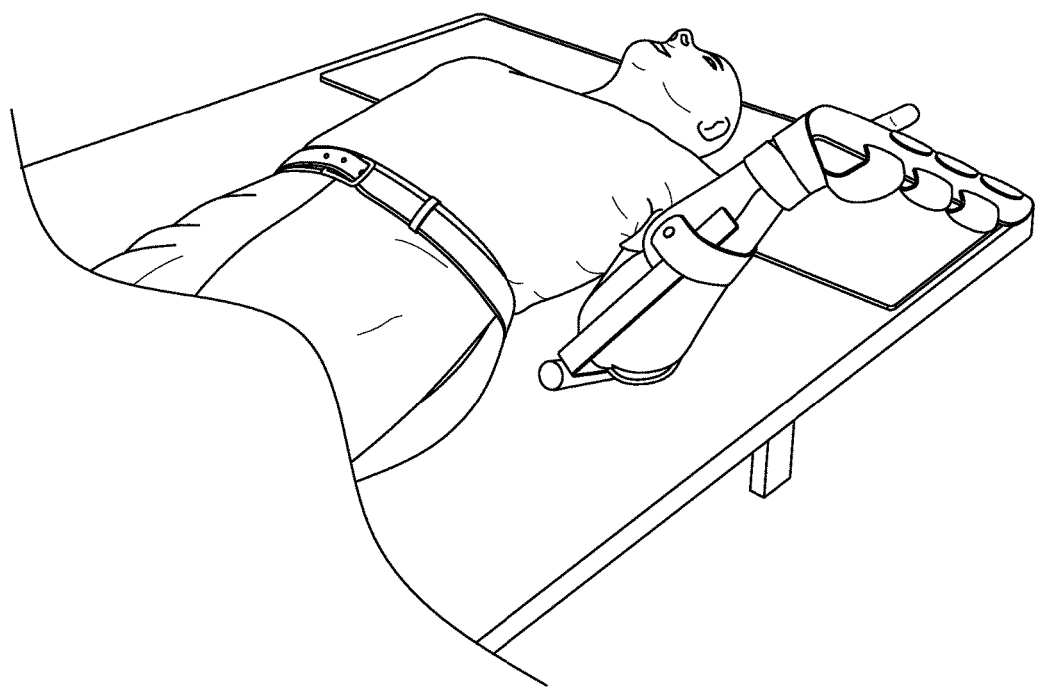
FIG. 14 illustrates a method of use of a rotation device.

The device 100 may be temporarily attached to the user's arm before or after the user lies down. Once the user is lying down, the user's arm may generally be positioned such that the elbow is near his waist or torso. The user may perform a shoulder rotation exercise which may comprise the user moving his arm in a rotational motion with his hand moving laterally away from his body. Beginning with FIG. 7, the user may start lying on his back with elbow generally near his waist. The user may then rotate his shoulder such that his hand and forearm move away from his torso, while the elbow generally remains in the same location, as shown in FIG. 8. The user may continue the rotational movement for as far as he desires, as shown in FIGS. 9-11. The user may then return his arm and hand to the beginning position, as shown in FIG. 7. This exercise is merely an illustration of one possible movement or exercise that may utilize the rotation device 100. There may be other movements or exercise that would benefit from the use of the rotation device 100, and the scope of the invention is not limited by the movements or exercises described herein. The user may also perform a shoulder rotation movement by beginning in position similar to that shown in FIG. 7 or 8, but moving his hand inwards towards his stomach, rotating at the shoulder and generally keeping the elbow at or near the starting position. Shoulder exercises or movements are also illustrated using straps 135 to at least partially secure the user's arm, hand, wrist, and/or fingers to the device, as shown in FIGS. 12-14.

Since the user may be lying on his back while using the device 100, the fulcrum portion 120 of the device 100 may contact or engage the structure on which the user is lying. Alternatively, the device 100 may be used by a user in other positions. For example, the user may start in a standing position with the device 100 generally attached to the user's arm as previously described. The user's arm may be rotated similar to that previously described. The rotation may be aided by a second person or through the use of a mechanical device.

A user performing the exercises and movements described herein may benefit from the rotation device 100 as described, because the rotation device 100 may aid the user in keeping parts of his body in the correct position during the exercises or movements. For example, the straps 135 on the rotation device 100 may keep the user's arm and/or hand in a specific position. Keeping the user's arm and hand in this position may facilitate a more effective rotational exercise.

The fulcrum portion 120 may allow the user's arm and shoulder to rotate more easily. One reason the fulcrum 120 may benefit the user's movement may be that it may raise the center of gravity of the user's arm higher above the table than if there was no fulcrum 120. Raising the center of gravity of the user's arm further above the table may produce greater leverage, which may aid the user's rotational movement. The lower arm portion 110 may be designed to keep the user's hand, wrist, and/or fingers in a specific position which may be beneficial to the rotational movement. For example, it may be beneficial for the user to keep his fingers in an extended position and the wrist flexed backward, as is shown in FIGS. 7-14. This position may keep the user from tightening up or otherwise constricting during the rotational movement. In addition, the straps 135 attached to the device 100 may help keep the hand, fingers, and/or wrist in this position, or may help keep the rotation device 100 engaged with the user's hands or arm during the movements or exercises. Keeping the user's hands and fingers in an extended position may help keep the hands and arm loose so that they do not interfere with shoulder movements.

In some embodiments the straps 135 may comprise tape (not shown). The tape may better secure the user's arm to the rotation device 100. In some instances, the user may benefit from his arm being more securely attached to the rotational device 100.

In some embodiments, the rotation device 100 comprises a connector 115 comprising a 90° bend 125. The user may benefit from the device 100 comprising a 90° bend 125 because that angle may keep the arm in a beneficial position. For example, if the user's arm was positioned at greater than a 90° angle, as measured at the elbow with the forearm generally being closer to the user's feet, then a different rotational movement may be encouraged. This may be undesirable as it may rotate the arm and shoulder in an undesirable motion or direction. For instance, if the user's arm is positioned at greater than a 90° angle the weight of the user's forearm and hand may have a tendency to rotate the user's arm about the fulcrum portion 120 or the connector 115, such that it may have a tendency to lift the user's upper arm up off of the surface, and away from the user's shoulder. Likewise, if the arm is positioned in at an angle that is less than 90°, such that the user's hand is closer to the user's head, this position may also create an unwanted rotation at the user's arm or shoulder. In this position, the arm may have a tendency to rotate such that the upper arm is pushed further into the table and may disrupt the desired rotation at the shoulder. Either of these additional rotational movements may be undesirable, if the user desires to rotate his shoulder in a specific rotational movement. By positioning the user's arm at approximately a 90° angle, the rotational movement may be isolated and the user may benefit from the isolated rotational movement.

The upper arm portion 105 and the lower arm portion 110 may comprise a plastic material, which may comprise a molded plastic material. The upper arm portion 105 and lower arm portion 110 may also comprise a metal or other material. In some embodiments the connector 115 and the fulcrum 120 comprise a metal, and may comprise a plastic or other material. The connector 115 and/or fulcrum portion 120 may comprise a metal bar, cylinder or other shape. The upper arm portion 105 and the lower arm portion 110 may be attached to the connector 115 using welding, adhesives, or other various attention means. In some embodiments, the fulcrum portion 120 is attached to the connector 115 by welding. However, the connector 115 may also attach to the fulcrum 120 by adhesives or other various attachment methods or systems.

In some embodiments the lower arm portion 110 may only at least temporarily attach to the connector 115 and may be adjustable. For instance, the lower arm portion 110 may comprise an adjustment mechanism wherein the lower arm portion 110 attaches to the connector 115 at one location 150 but may be detached and reattached at a second location 155. The second location 155 may position the lower arm portion 110 closer or further away from the fulcrum portion 120. The adjustment mechanism may allow the rotation device 100 to be better fit to the dimensions of the user's arm. For example, a user with longer arms may benefit from the lower arm portion 110 being positioned further away from the fulcrum 120. Or, a user with shorter arms may benefit from the lower arm portion 110 being closer to the fulcrum 120. The upper arm portion 105 may be adjustable as compared to the connector 115 as well. For instance, the upper arm portion 105 may be adjustable such that the upper arm portion 105 is closer or further away from the 90° angle.

In some embodiments, the rotation device 100 may be specific to which side of the body with which the user is to use the device. For instance, a first rotation device 100 may be used with a user's right arm, and a second rotation device 100 may be used with the user's left arm. In some embodiments at least part of the rotation device 100 may be used with both of the user's arms. For instance, the upper arm portion 105, connector 115, and fulcrum 120 may be used with both the user's left and right arms, and the lower arm portion 110 may be interchangeable and replaceable depending on which arm the user is exercising.

Terminology: Additional Embodiments

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. Additionally, a person having ordinary skill in the art will readily appreciate, the terms "upper" and "lower" are sometimes used for ease of describing the figures, and indicate relative positions corresponding to the orientation of the figure on a properly oriented page, and may not reflect the proper orientation of the device as implemented.

Certain features that are described in this specification in the context of separate implementations also can be implemented in combination in a single implementation. Conversely, various features that are described in the context of a single implementation also can be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

In describing the present technology, the following terminology may have been used: The singular forms "a," "an," and "the" include plural referents unless the context clearly dictates otherwise. Thus, for example, reference to an item includes reference to one or more items. The term "ones" refers to one, two, or more, and generally applies to the selection of some or all of a quantity. The term "plurality" refers to two or more of an item. The term "about" means quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3 and 4 and sub-ranges such as 1-3, 2-4 and 3-5, etc. This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. Conjunctions, such as "and," "or" are used interchangeably and are intended to encompass any one element, combination, or entirety of elements to which the conjunction refers.

What is claimed is:

1. A device for increasing shoulder mobility in a person, consisting of:
    an upper portion configured to attach to a person's upper arm;
    a lower portion configured to attach to a person's lower arm and open palm such that the open palm and the lower arm are held in a fixed position relative to the upper arm;
    a connector joining the upper and lower portions, wherein the connector is positioned at an angle; and
    a cylinder fixedly coupled to the connector along a length of the cylinder, the cylinder abutting the connector opposite the upper portion to support continuous manual rotational motion of the device about the cylinder while the length of the cylinder is resting on a planar surface,
    wherein the upper and lower portions position the person's upper and lower arms at a fixed angled position that facilitates movement of the shoulder.

2. The device of claim 1, wherein the upper portion comprises a surface that cradles or otherwise engages the upper arm.

3. The device of claim 2, wherein the surface is shaped as a trough or a semi-cylinder.

4. The device of claim 1, wherein the lower portion is configured to isolate the person's hand or wrist in a specific position.

5. The device of claim 1, wherein the lower portion is configured to keep the person's fingers extended and the person's wrist flexed backward.

6. The device of claim 1, wherein the lower portion comprises a hand section that engages a person's hand or wrist.

7. The device of claim 6, wherein the hand section comprises a curved surface that wraps around at least a part of the person's hand.

8. The device of claim 1, wherein the cylinder is configured to raise a center of gravity of an arm of the person when the person is in a supine position.

9. The device of claim 1, wherein a longitudinal axis of the cylinder is aligned with a portion of the connector to which the upper portion is connected.

10. The device of claim 1, further comprising one or more straps configured to encircle at least part of an arm or a hand of the person.

11. The device of claim 10, wherein the one or more straps are disposed on the upper portion or the lower portion.

12. The device of claim 1, wherein the connector comprises a bend that is 90°.

13. The device of claim 1, wherein a position of the lower portion on the connector is adjustable.

14. The device of claim 12, wherein the connector has a first location spaced apart from a second location, each of the first and second locations being configured for attachment with the lower portion, the lower portion being positioned further away from the cylinder when the lower portion is attached to the first location than when the lower portion is attached to the second location.

* * * * *